US012708693B2

(12) United States Patent
Slotkin et al.

(10) Patent No.: US 12,708,693 B2
(45) Date of Patent: Aug. 18, 2026

(54) AIR/SURFACE CLEANING APPARATUS PARTICULARLY CONFIGURED FOR UNDER-SEAT INSTALLATION AND OPERATION WITHIN AN OCCUPIED PASSENGER BUS

(71) Applicant: Radical Clean Solutions Ltd., Long Beach, NY (US)

(72) Inventors: Roger Slotkin, Long Beach, NY (US); Ralph T. Kubitzki, Plantation, FL (US)

(73) Assignee: Radical Clean Solutions Ltd., Long Beach, NY (US)

( * ) Notice: Subject to any disclaimer, the term of this patent is extended or adjusted under 35 U.S.C. 154(b) by 699 days.

(21) Appl. No.: 18/075,755

(22) Filed: Dec. 6, 2022

(65) Prior Publication Data

US 2023/0173131 A1 Jun. 8, 2023

Related U.S. Application Data

(63) Continuation-in-part of application No. 17/861,181, filed on Jul. 9, 2022, now Pat. No. 12,594,356, and a (Continued)

(51) Int. Cl.

*A61L 9/20* (2006.01)
*A61L 2/10* (2006.01)
*B60H 3/00* (2006.01)

(52) U.S. Cl.

CPC *A61L 9/20* (2013.01); *A61L 2/10* (2013.01); *B60H 3/0078* (2013.01)

(58) Field of Classification Search

CPC ........ A61L 2/10; A61L 9/20; A61L 2209/111; A61L 2209/12; A61L 2209/15; A61L 2209/20

See application file for complete search history.

(56) References Cited

U.S. PATENT DOCUMENTS 2,945,554 A 7/1960 Berly
5,968,455 A * 10/1999 Brickley .................. A61L 9/20 362/267

(Continued)

FOREIGN PATENT DOCUMENTS

JP 2010080195 A 4/2010
WO PCT/US2022/051886 A 5/2023

OTHER PUBLICATIONS

LSE (Light Spectrum Enterprises); "Shop UV Lighting-GPH457T5L/4P Ultraviolet UV Lamp Bulb 4-pin Base 18" GPH457T5"; 1300 Industrial Blvd.—Ste B3, Southampton, PA 18966.

(Continued)

*Primary Examiner* — Timothy C Cleveland
(74) *Attorney, Agent, or Firm* — Alfred M. Walker; Thomas A. O'Rourke; James Bongiorno

(57) ABSTRACT

A system for decontaminating/neutralizing breathable air and surfaces in an occupied enclosed space, i.e., hydroponic greenhouses, aircraft, rail and road vehicles, in building ducts, or rooms, includes mounting an atmospheric hydroxyl radical generator along an inside surface of an occupied space having respective air inlets and air outlets. The hydroxyl radical generator includes a polygonal housing supporting a plurality of spaced crystal-spliced UV optics medical grade pure quartz, which emit/irradiate ultraviolet in the nanometer wavelength/ultraviolet spectrum of between 100 and 400 nanometers for deactivating and neutralizing atmospheric chemicals and pathogens in breathable air and surfaces. The hydroxyl radicals contact the walls of the reaction chamber housing. The hydroxyl radicals become created and excited to react quickly with impurities including VOC, virus, bacteria and fungi, rendering them inactivated and neutral. The breathable air passes through the polygonal housing and is decontaminated and neutral- (Continued)

ized of impurities before entering the occupied enclosed space.

8 Claims, 14 Drawing Sheets

Related U.S. Application Data continuation-in-part of application No. 17/826,555, filed on May 27, 2022, now abandoned, and a continuation-in-part of application No. 17/713,959, filed on Apr. 5, 2022, now Pat. No. 12,246,116, which is a continuation-in-part of application No. 17/674,763, filed on Feb. 17, 2022, now Pat. No. 12,390,547, said application No. 17/826,555 is a continuation-in-part of application No. 17/590,270, filed on Feb. 1, 2022, which is a continuation-in-part of application No. 17/545,919, filed on Dec. 8, 2021, said application No. 17/861,181 is a continuation-in-part of application No. 17/545,919, filed on Dec. 8, 2021, said application No. 17/674,763 is a continuation-in-part of application No. 17/545,919, filed on Dec. 8, 2021.

(56) References Cited

U.S. PATENT DOCUMENTS 6,497,840 B1 12/2002 Palestro et al.
6,613,277 B1 9/2003 Monagan
6,805,733 B2 10/2004 Engel et al.
7,416,588 B2 * 8/2008 Burrows .................. A61L 9/20 422/24
7,837,933 B2 11/2010 Sevack et al.
7,976,195 B2 7/2011 Engel et al.
7,988,923 B2 8/2011 Fink et al.
8,252,099 B2 8/2012 Worrilow
8,252,100 B2 8/2012 Worrilow
8,545,753 B2 10/2013 Sevack et al.
8,747,753 B2 6/2014 Engel et al.
9,168,323 B2 10/2015 Morneault
9,522,210 B2 12/2016 Worrilow
9,675,725 B2 6/2017 Worrilow
9,884,135 B2 2/2018 Bystrzynski et al.
9,956,306 B2 5/2018 Brais et al.
9,980,748 B2 5/2018 Worrilow
10,857,249 B2 12/2020 Brais et al.
11,103,611 B2 8/2021 Elde et al.
2008/0073565 A1 3/2008 Jeon
2015/0114822 A1 4/2015 Greco
2017/0225973 A1 8/2017 Henderson et al.
2020/0084983 A1 3/2020 Liang et al.
2020/0129972 A1 4/2020 Ozaki et al.
2021/0339184 A1 * 11/2021 Hourani .................... F24F 8/10

OTHER PUBLICATIONS

Hao Chen, et al.; "A Hydroxyl radical detection system using gas expansion and fast gating laser-induced fluorescence techniques"; The Research Center for Eco-Environmental Sciences, Chinese Academy of Sciences; Journal of Environmental Sciences 65 (2018) 190-200; published by Elsevier B.V.; http/dx.doi.org/10.1016/i.jes.2017.03.012.

* cited by examiner

HVAC Unit Block Diagram

Consumer Unit Block Diagram

700
Vehicle DC Power
728
760a
120
701
719
770a
713
711
712

700
701
728
120
719
713
Air In
Air Out
760a
770a
711
712
770b
760b

AIR/SURFACE CLEANING APPARATUS PARTICULARLY CONFIGURED FOR UNDER-SEAT INSTALLATION AND OPERATION WITHIN AN OCCUPIED PASSENGER BUS

RELATED APPLICATIONS

This application is a continuation-in-part (CIP) of application Ser. No. 17/861,181 filed Jul. 9, 2022, which '181 application is a continuation-in-part (CIP) of application Ser. No. 17/545,919 filed Dec. 8, 2021. This application is also a continuation-in part (CIP) of application Ser. No. 17/713,959 filed Apr. 5, 2022, which '959 application is a continuation-in-part (CIP) of application Ser. No. 17/674,763 filed Feb. 17, 2022, which '763 application is a continuation-in-part (CIP) of application Ser. No. 17/545,919 filed Dec. 8, 2021. This application is also a continuation-in-part (CIP) of application Ser. No. 17/826,555 filed May 27, 2022, which '555 application is a continuation-in-part (CIP) of application Ser. No. 17/590,270, filed Feb. 1, 2022, which '270 application is a continuation-in-part (CIP) of application Ser. No. 17/545,919 filed on Dec. 8, 2021. The '919, '270, '763, '959, '555 and '181 are each incorporated by reference herein. Applicant claims priority under 35 USC § 120 from the 919, '270, '763, '959, '555 and '181 applications.

FIELD OF THE INVENTION

The present invention relates use of a harmonic bio-mimicry nonchemical photonic process that results in the export of desired atmospheric hydroxyls at precisely the same rate as nature provides (2.6 million per cubic Centimeter—NASA), to neutralize toxic chemicals and pathogens in breathable air/surfaces in stationary or moving human occupied spaces.

BACKGROUND OF THE INVENTION

Ultraviolet light (UV) delivery in the form of directing ultraviolet light on unsanitary surfaces as germicides, bactericides and viricides are disadvantageous because, upon exposure to breathable air in mass transit rail and road vehicles, as well as aircraft and related airborne vehicles, such as helicopters, seating fabrics in building interior ducts and wall surfaces and other human occupied spaces, the ultraviolet light compromises fabrics and doesn't penetrate into crevices between, or in, passenger seats or flight deck seats, located in the flight deck, separately sealed away from the air of the passenger cabin, or in seating fabrics in mass transit rail and road vehicles, in building interior ducts and wall surfaces, in hydroponic greenhouses, in portable room-sized units and other human occupied spaces. Delivery of ultraviolet light for sanitation is limited because the ultraviolet light is only as effective as the actual line of sight of the ultraviolet waves.

DESCRIPTION OF THE PRIOR ART

Methods of Producing Atmospheric Hydroxyls

In the field of physics there are, to date, only a few processes in a device that generates an atmospheric hydroxyl that purportedly are useful in removing contaminants from breathable air. In theory the NASA device produces the hydroxyl in a photo catalytic oxidation (PCO) process, by emitting an ultraviolet irradiation of 254 nanometers as it interfaces with titanium dioxide ($TiO_2$) plating. In theory, the hydroxyl is produced only at the interface site of contact at the surface of the $TiO_2$. The hydroxyl does not exit the airstream and does not have any downstream interaction. Minimal air flow must be maintained at approximately 120 cfm. Typical HVAC systems utilize faster air movement at approximately 2000 cfm and this would not allow for the theoretical hydroxyl to form.

OBJECTS AND SUMMARY OF THE INVENTION

This Summary is provided to introduce a selection of concepts in a simplified form that are further described below in the Detailed Description of the Drawings. This Summary is not intended to identify key features or essential features of the claimed subject matter, nor is it intended to be used to limit the scope of the claimed subject matter.

In contrast, the present invention uses airborne hydroxyl radical molecules, which are of very small molar size and can occupy almost any given space. They can occupy dark crevices that ultraviolet line of sight cannot get access to. The present invention allows for a "Harmonic" of photonic UV frequencies to be applied within a hydroxyl producing reaction chamber. The feed stock is ambient water vapor in air which will have relative humidity, this humidity is the feed stock for the reaction chamber to produce the atmospheric hydroxyl.

This action is called "Bio-Mimicry". The present invention process is a totally green, environmentally friendly nonchemical process that results in the export of the desired atmospheric hydroxyl at precisely the same rate as nature provides, namely, at 2.6 million per cubic centimeter. The atmospheric hydroxyl process begins by exposing ambient water vapor to special UV optics having hydroxyl activation portions made of medical grade pure quartz material. The optics are designed to emit/irradiate Ultraviolet irradiation in the nanometer wavelength/Ultraviolet spectrum of between 100 and 400 nanometers, thereby producing the hydroxyls at the aforementioned quantity of 2.6 million hydroxyls per cubic centimeter, as provided in nature. This is a novel improvement over prior art NASA PCO based technology.

Hydroxyl are groups having the radical "—OH" and are represented by the symbol —OH or HO—, which can have a negative charge or be neutral. The hydroxyl functional group includes one hydrogen atom which is covalently bonded to one oxygen atom. Hydroxyl radicals are very reactive, which react quickly to hydrocarbons, carbon monoxide molecules and other air impurities, such as volatile organic compounds, (VOC), virus, bacteria and fungi.

Many closed HVAC air systems can harbor microscopic bacteria, virus (i.e., Covid-19) and fungi.

For example, aircraft and other airborne transportation vehicles, such as helicopters, seat fabrics on mass transit rail and road vehicles, in building ducts and wall surfaces, in hydroponic greenhouses, and other human occupied spaces, can harbor bacteria and virus in the separate, circulated air systems.

Also, residential rooms in dwellings or assisted living communities can harbor bacteria and virus in the separate, circulated air systems.

Therefore, the present invention is a unique and novel application method for the delivery of safe and natural hydroxyl radicals into breathable air volume containers such as agricultural hydroponic greenhouses and the agricultural plant contents therein, airline flight deck or passenger cabins, and the contents therein, seat fabrics on mass transit rail and road vehicles, in building HVAC ducts and the breathable ambient or heated or cooled air flow contents therein. To be considered as well are upholstered chair seats, benches, contact surfaces such as grab bars, handles in building wall surfaces and other human occupied spaces.

In the present invention, the atmospheric hydroxyl radicals are generated in closed multi-sided housing, preferably polygonal, having therein two or more parallel UV optics which are multi segmented with crystal, so that when enabled, the hydroxyl radicals are generated. Hydroxyls are reactive and short lived, however the closed housing reaction chamber preferably has polygonal interior walls, so that the hydroxyl radicals will bounce against the walls so as to decontaminate within the reaction chamber as well as downstream in open air areas. Breathable air is then directed through the closed housing, so that the created and excited radicals will react quickly to air and surface impurities, such as pathogens and VOC's, rendering them neutral.

The UV optics are tubular, medical grade pure quartz. The optics are designed to emit/irradiate Ultraviolet irradiation in the nanometer wavelength/Ultraviolet spectrum of between 100 and 400 nanometers.

A multi wave 'Harmonic' is created via a multiwavelength nanometer configured optic irradiation. This configuration results in the creation of the desired atmospheric hydroxyl within the hydroxyl generator reaction chamber, which is a multi-sided reaction chamber, designed in such a way as to optimize atmospheric downstream hydroxyl production, such as for example in a polygonal-shaped housing. This multi-sided reaction chamber enables the desired atmospheric hydroxyl to be injected downstream to affect positive change. The positive change is the control/neutralization of pathogens and VOC's.

The —OH formed hydroxyl molecule is the capacitor that donates electrons to the targeted pathogen, whereupon the pathogen is therefore neutralized by the 'Electron Voltage (eV')' capacitance carried by the hydroxyl. The eV is donated at the point of contact with the pathogen.

VOC's are neutralized through the action of Bond Dissociation Energy (BDE). The capacitance of the charged hydroxyl is sufficient so as to take out of phase (decomposition) of any airborne molecular or compound structure. In Phase VOC chemistry can be harmful, therefore out-of-phase atomic airborne structures are now neutral and cannot recombine. The exception to this rule would be the recombination of water vapor, carbon dioxide and lastly oxygen (O2).

This reaction sequence is essential to all life, in that water vapor feeds all life, and carbon dioxide (CO2) is necessary/essential for plant life and oxygen (O2) is essential for air breathers such as humans, other animals and forms of living organisms.

Because exposure of the UV light is problematic for human eyes, the interior of the reaction chamber is custom designed to arrest UV light escaping and to maximize atmospheric hydroxyl discharge. Refraction color can come out of the unit with the generated, activated hydroxyls, but never direct UV light.

Available hydrogen is low in our natural environment, so one must add electron rings to obtain optimal amplitude as opposed to adding hydrogen for increased hydroxyl production.

The polygonal shape of the reaction chamber enhances the total ability of the chamber to produce the desired atmospheric hydroxyl.

It is essential that the atmospheric hydroxyls be produced by the exposure of ambient water vapor within a confined refractive generator chamber housing to prevent diminution of the atmospheric hydroxyls. In contrast, SanUVox, by using outward facing reflectors but no confined generator chamber housing, causes a drastic diminution of the desired hydroxyl production.

In contrast the present invention, by using the polygon shaped reaction chamber, has categorically enhanced atmospheric hydroxyl production.

Because exposure of the UV light is problematic for human eyes, the interior chamber holding the reaction chamber is custom designed to arrest UV light escaping and to maximize atmospheric hydroxyl discharge. Refraction color can come out of the unit with the generated, activated hydroxyls, but never direct UV light.

Available hydrogen is low in our natural environment, so one must add electron rings to obtain optimal amplitude as opposed to adding hydrogen for increased hydroxyl production.

The polygonal shape of the reaction chamber enhances the total ability of the chamber to produce the desired atmospheric hydroxyl.

It is essential that the atmospheric hydroxyls be produced by the exposure of ambient water vapor within a confined refractive generator chamber housing to prevent diminution of the atmospheric hydroxyls. In contrast, the prior art of SanUVox, by using outward facing reflectors but no confined generator chamber housing, causes a drastic diminution of the desired hydroxyl production.

In contrast the present invention, by using the polygon shaped reaction chamber, has categorically enhanced atmospheric hydroxyl production.

However, in small environments, such as in a self-contained unit in a transit vehicle (passenger rail, passenger bus, trucking cargo shipping, etc.), or in a portable room size self-contained unit (movable with casters or wheels, or stationary mounted to a room surface, such as a wall), a fan is necessary to pull the ambient air with water vapor into the polygonal hydroxyl generator with a UV quartz optics, so that the water vapor molecules become hydroxyl radicals and thereafter are pushed by the fan out of the self-contained and/or portable unit.

For safety, an air pressure safety switch is provided, so that when air flow is not detected, this unit will be dormant. A Micro Switch shuts down all systems should the device be opened when unit is in the ON/RUN position.

Transit Vehicles Device and System

The transit vehicle unit also has a unique Internal Air Baffling System, to promote the zig zag of air movement therein, to control light and prevent unwanted UV light from escaping so that the breathable air passes through the transit vehicle unit. The unique device design does not allow for any UV light to exit the unit.

The transit vehicle units were targeted to emulate certain characteristics required within the hospital framework. Pathogen and VOC control is of paramount concern and is inherent within the design parameters of the hydroxyl generating device. Consideration was also made with regard to sound control, wherein low air flow volume of 110 cubic feet (of) must be quieter than 30 decibels or below (Hospital Quiet).

The transit vehicle units also contain an optimal-UV light refraction tubular fan assembly, which draws in the incoming air into the hydroxyl generator chamber housing. Baffles located in the transit vehicle and duct installed hydroxyl generators allow air through the hydroxyl generator but prevent exposed UV light from escaping. The sole purpose of the baffles is to arrest any UV rays from escaping the device. Any direct line of sight to the UV source would cause a "Welders Flash" incident and may temporarily harm the eyes of the observer. This type of incident is simply not allowed and is part of the safety investigation of the validation bodies UL/CSA.

The transit vehicle units also have communications capabilities, so that the Hydroxyl Generating Device can interface with a remote-control pad or mobile phone.

Safety features include a microswitch which will shut off from inadvertent opening if the reaction chamber device is "on" when it should be "off". The micro switch shuts down all systems should the device be opened when the generating unit is in operational status.

Anti-Vibration G-Force Mitigation Clips are installed, such as spring clips which operate in only one directional installation.

Reactor Rod Safety is paramount, for prevention of Reactor Rod displacement and breakage.

The transit vehicle unit also includes custom designed noise reduction adhesive pads, and strategically placed self-adhesive sound/vibration reduction material wall insulation to mitigate sound and vibration.

The transit vehicle hydroxyl generating units in general have the above features, but where the optics may optionally be provided in a two optic array of a-b options, where "A" is on, but "B" is on if A fails.

Because the transit vehicle hydroxyl generator is a self-contained, small unit, a fan assembly is needed to send air in and out of the hydroxyl generator unit for transit vehicles. Where optionally there is provided a double optic option one optic may be on to create the hydroxyl radicals with the dual optic availability, should there be an abnormal intrusion of VOCs' or pathogens into the transit vehicle hydroxyl generator, then the sensor would alert the hydroxyl device and the second optic would then come online in order to neutralize the threat load.

The hydroxyl generator includes a housing having an air inlet at one end and air outlet at an opposite end thereof, wherein the housing contains a plurality of spaced crystal-spliced UV optics, the UV optics being tubular, medical grade pure quartz optics designed to emit/irradiate ultraviolet in the nanometer wavelength/ultraviolet spectrum of between 100 and 400 nanometers for deactivating chemicals and pathogens in the breathable air for the respective flight deck and passenger compartments, on mass transit rail and road vehicles, in building ducts and other human occupied spaces. The air inlet at one end and the air outlet at an opposite end of the housing are provided for exposing ambient water vapor to the plurality of spaced crystal-spliced UV optics, to generate the hydroxyls. Preferably, the housing comprises a lengthwise extending hollow housing having a polygon shape in cross section, with adjoining lengthwise extending flat walls.

In summary the hydroxyl generator includes a housing having an air inlet at one end and air outlet at an opposite end thereof, wherein the housing contains a plurality of spaced crystal-spliced UV optics, the UV optics being tubular, medical grade pure quartz optics designed to emit/irradiate ultraviolet in the nanometer wavelength/ultraviolet spectrum of between 100 and 400 nanometers for deactivating chemicals and pathogens in the breathable air for the respective flight deck and passenger compartments, on mass transit rail and road vehicles, in building ducts and other human occupied spaces. The air inlet at one end and the air outlet at an opposite end of the housing are provided for exposing ambient water vapor to the plurality of spaced crystal-spliced UV optics, to generate the hydroxyls. Preferably, the housing comprises a lengthwise extending hollow housing having a polygon shape in cross section, with adjoining lengthwise extending flat walls.

BRIEF DESCRIPTION OF THE DRAWINGS

The present invention can best be understood in connection with the following drawings, which are not deemed to be limiting in scope.

FIG. 6B also shows a fan unit in the housing to expel the newly purified air from the working operation of the polygonal hydroxyl generator unit and transferring the air through a grate in the outer self-contained housing of the hydroxyl generator.

DETAILED DESCRIPTION OF THE DRAWINGS

As used throughout this specification, the word "may" is used in a permissive sense (i.e., meaning having the potential to, or being optional), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, It is noted that the citing of any reference within this disclosure, i.e., any patents, published patent applications, and non-patent literature, is not an admission regarding a determination as to its availability as prior art with respect to the herein disclosed and claimed apparatus/method.

Furthermore, any reference made throughout this specification to "one embodiment" or "an embodiment" means that a particular feature or characteristic described in connection therewith is included in at least that one particular embodiment.

Thus, the appearances of the phrases "in one embodiment" or "in an embodiment" in various places throughout this specification are not necessarily all referring to the same embodiment. Therefore, the described features, advantages, and characteristics of any particular aspect of an embodiment disclosed herein may be combined in any suitable manner with any of the other embodiments disclosed herein.

Figures 1, 2:
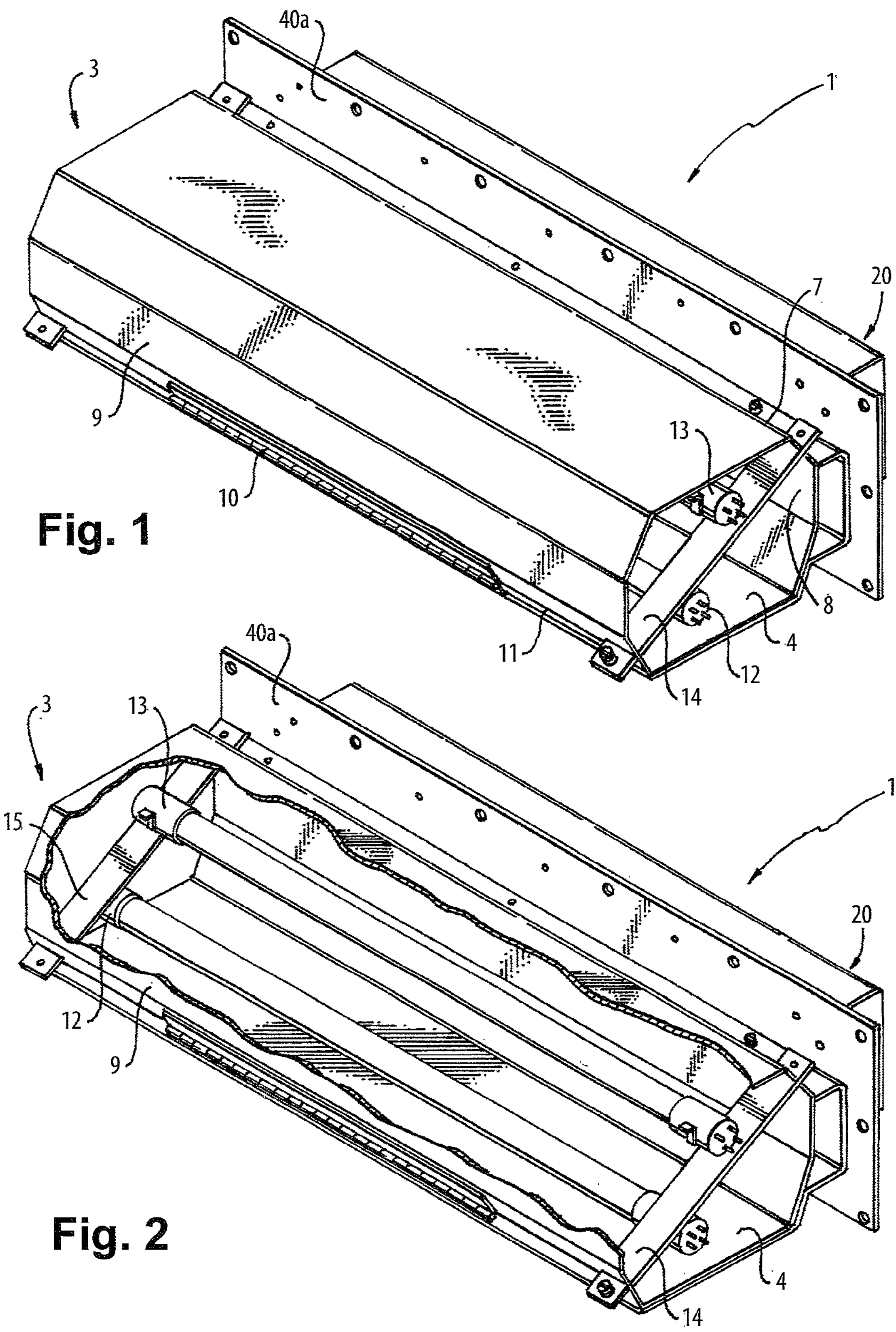
FIG. 1 is a perspective view of a polygonal hydroxyl generator shown in a closed position.
FIG. 2 is a perspective view of the hydroxyl generator of FIG. 1 shown in partial cross section with an open view of the interior of the hydroxyl generator.

FIG. 1 shows a hydroxyl generator 1, including a polygonal-shaped housing, including a bracket brace 14 for supporting crystal-spliced UV optics 12 and 13 within respective C-shaped spring clasps 12*a* and 13*a*, which are each respectively mounted on bracket brace 14, which are mounted parallel lengthwise to each other inside the clamshell hexagon housing, but staggered so that UV optic 12 is on a different side of the bracket 14 from the side on which UV optic 13 is located, wherein the crystal spliced UV optics 12 and 13, each have a length that runs substantially the entire length of the housing of the hydroxyl generator 1. A preferred example for the crystal-spliced UV optics 12 and 13 is the GPH457T5L/4P UV Optic 4-pin Base 18" GPH457T5 of Light Spectrum Enterprises of Southampton; these optics 12 and 13 are typically 18 inches long and are made of quartz. The tubular optics 12 and 13 are composed of pure Medical Grade quartz crystal in the portion of the optics which creates the hydroxyls. The present invention adds additional frequencies to the pure crystal optics. These tubular optics 12 and 13 generate 'Harmonic' bio-mimicry nonchemical process of the present invention which enables the production of desired atmospheric hydroxyls at a rate commensurate with the VOC/Bio loading in that particular space to be treated with the hydroxyls.

In contrast to the medical grade quartz tubular optics, it is noted that total glass tubes cannot be used when generating UV. The glass would simply be vaporized. Some companies use a fusion of glass and quartz crystal, which is not optimal as the glass portion creates a frequency that actually attracts contaminants. This problematic action neutralizes the desired UV action. Such a fusion lamp of glass and quartz crystal is cheaper to produce, however the poor performance of the lamp would be the end result.

Figure 3:
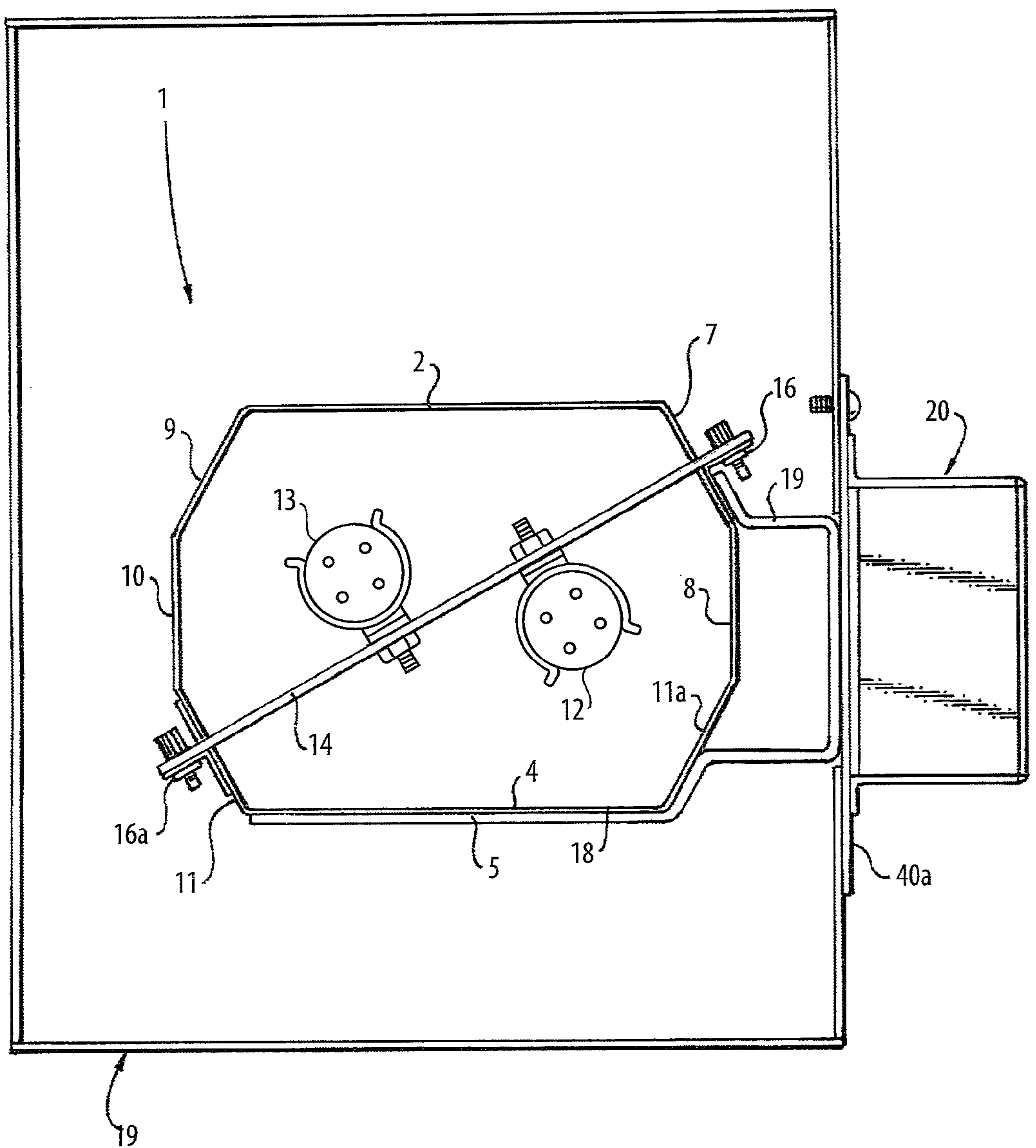
FIG. 3 is an end view in cross section of the hydroxyl generator of FIG. 1, with two UV optics for generating hydroxyl radicals.
Figure 4:
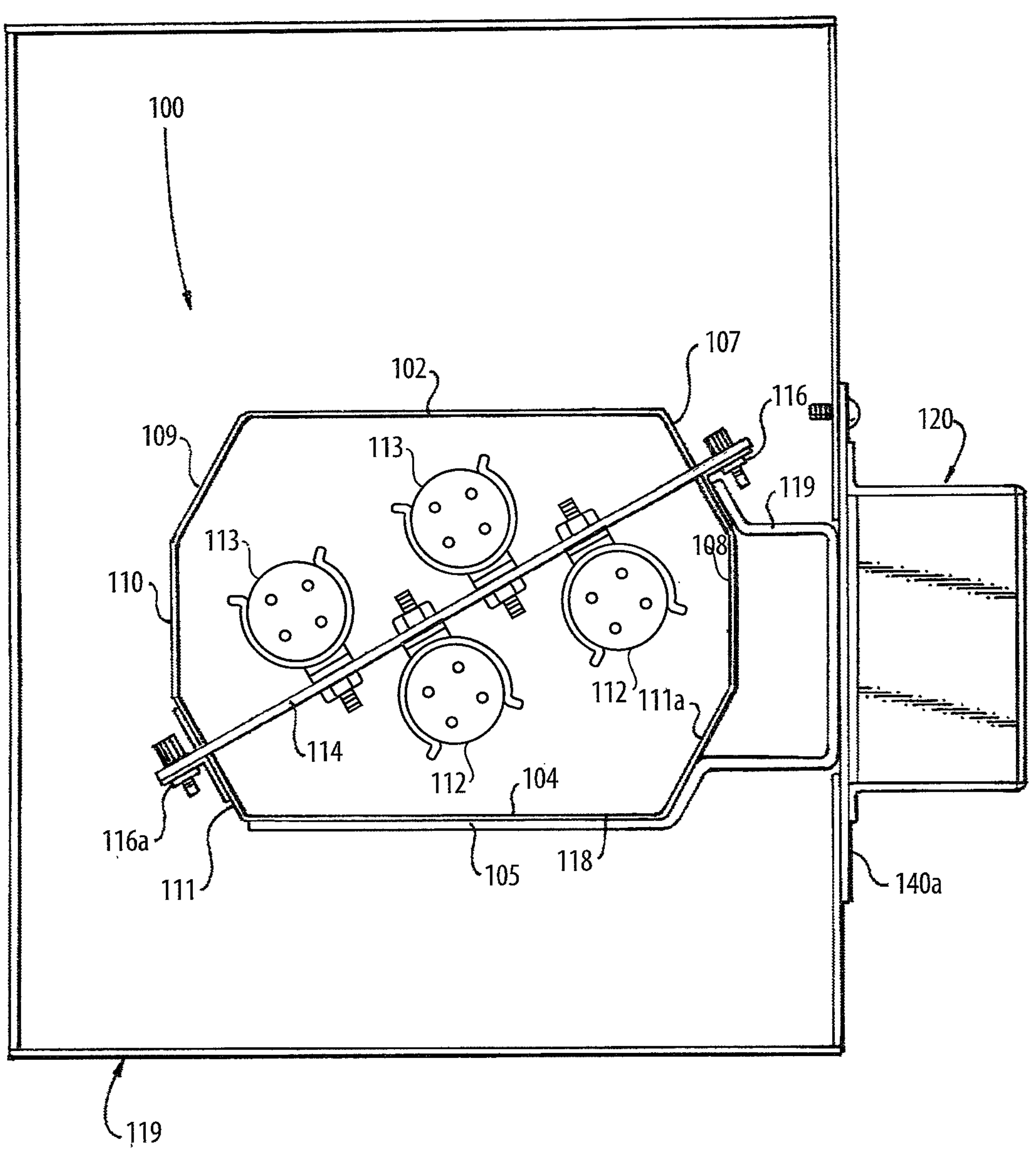
FIG. 4 is a cross sectional end view of an alternate embodiment for a hydroxyl generator, showing four UV hydroxyl generator optics within the polygonal hydroxyl generator.

Other similar Medical Grade quartz tubed UV optics can be used. The optics 12 and 13 are preferably symmetrically positioned in the housing of the hydroxyl generator 1, as shown in FIGS. 3 and 4 to operate most efficiently, but where in FIG. 3 the crystal spliced UV optics 12 and 13 are staggered so that UV optic 12 is on a different side of the bracket brace 14 from the side on which UV optic 13 is located. FIG. 4 shows an alternate embodiment where there are two pairs of UV optics, namely 112,112 and 113, 113. The UV optics 112, 112 are staggered to the right on one bottom side of the horizontal bracket brace 114, but are separated by upright bracket brace 114. Likewise, UV optics 113 and 113 are respectively staggered to the left on the opposite top side of the horizontal bracket brace 114, also separated from each other by upright bracket brace 114. Optics pairs 112, 112 and 113, 113 are supported within pairs of respective C-shaped spring clasps, which pairs of optics 112, 112 and 113, 113 are each respectively mounted on bracket brace 114, and which pairs of optics 112, 112 and 113, 113 are mounted parallel lengthwise to each other inside the clamshell hexagon housing 1.

The clamshell hexagon housing hydroxyl generator 1 has a clamshell configuration, including a clamshell top wall 2, upper side walls 7, 8, 9 and 10, fasteners 16*a*, 16*a*, a hinge 6 for opening the polygonal clamshell housing 1 and a bottom clamshell portion, including a bottom wall 4 and angle-oriented walls 11 and 11*a*, whereby the polygon housing opens hinge 6 to expose the inside of the hydroxyl generator 1 for maintenance and/or repair. In addition, the polygon hydroxyl generator enclosure can be removed from the air duct wall 40A for such maintenance and repair. The hydroxyl generator also includes an adjacent electronic control box 20, which is attachable to the clamshell housing of the hydroxyl generator 1. Alternatively, as shown in FIGS. 3 and 4, the electronic control box 20 is preferably located outside of the air path, which may be a duct or other conduit. It can alternatively be attached outside of the duct. It communicates with the UV optics wirelessly. The reason for the polygon shape is that the hydroxyl generators generated by the crystal-spliced UV optics 12 and 13 are scattered upon being generated by the optics 12 and 13, but they dissipate quickly if not activated by contact with reflective non-absorbent surfaces inside the respective walls of the polygon. The purpose of the polygon shape is that when the hydroxyl radicals are generated, they are emitted radially in all directions from the UV crystal-spliced optics 12 and 13 and normally would dissipate when scattered radially from the optics. In order to permit the hydroxyl radicals to maintain their desired electron charge and ability to contact and inactivate mold, volatile organic compounds, pathogens, bacteria, virus, etc., they need to reflect and refract off of the reflective non-absorbent walls continuously, within the reaction chamber confined space. As atmospheric hydroxyls are being activated by being created and excited in back-and-forth activity, the air inside the air duct/plenum 40*a* will contact the activated hydroxyl radicals with the end result of the neutralization of any impurities, such as VOCs, virus, bacteria, fungi, etc., in the air and surfaces.

Furthermore, once these radicals are emitted, they can penetrate any crevices in any area, such as in hydroponic greenhouse plant media growing vessels, such as between seats of aircraft, mass transit rail and road vehicles, in building ducts and wall surfaces and other human occupied spaces, such as individual rooms with small self-contained hydroxyl generators, between the surfaces of seats and shelving, and anywhere where ultraviolet light by itself would not be capable of eradicating the undesirable VOCs, fungi, virus, bacteria, etc. In the aircraft environment, the polygon-shaped housing is strategically located within an air supply unit in an airport terminal building, or it can be located within a remote cart not located near the aircraft, on the tarmac of the airport, and preferably it may be provided in the air systems separately of an aircraft cabin, including the flight deck and the areas of the main cabin where passengers are seated. Therefore, the polygon shaped housings may also be strategically located in mass transit rail and road vehicles, in building ducts, in individual rooms, and wall surfaces and other human occupied spaces As shown in the end view of FIG. 3, the inside of the polygon housing 1 is located below the field of vision within the sealed off plenum so that the ultraviolet (UV) crystal-spliced tubular optics 12 and 13 will not be exposed to the eyes of any observers. Therefore, while the hydroxyl radicals are being generated, the UV energy which create hydroxyl generation from optics 12 and 13 are completely sealed off so that when the optics 12 and 13 are operational, the UV light emanating therefrom will not penetrate outside of the polygonal housing. Baffles, optionally located outside of the hydroxyl generators, but in the vicinity of the hydroxyl generators, prevent the UV light from exposure to persons. Additionally, fibrous filters may be provided at input and outlet areas of the housing containing the hydroxyl generator portion with the UV optics, to capture any undesirable airborne particulates, such as dirt and dust and other particles which may compromise the sensitive quartz material of the UV optics. There is no restriction regarding the active flow of the hydroxyls inside the hydroxyl generator 1 and no interference with the excitement of the hydroxyls produced by the exposure of ambient water vapor within the polygon shaped housing with the UV optics 12 and 13 irradiating light that causes the —OH radicals to form.

FIG. 4 shows an alternate embodiment for a four optic version, where polygon hydroxyl generator enclosure 100, having top wall 102, side walls 107, 108, 109, 110 of an upper shell, as well as lower walls 105, 111*a*, 111*b* of the clamshell housing. The clamshell housing has inner wall surfaces 104 against which the hydroxyls being formed contact repeatedly during formation. FIG. 4 also shows the electronics control box 120, attached to the clamshell housing by brackets 119. The respective pairs of optics 112, 112, and 113, 113 are supported within respective pairs of C-shaped spring clasps, which are each respectively mounted on bracket brace 114, which are mounted parallel lengthwise to each other inside the clamshell hexagon housing 101. The upper half of the clamshell housing is connected to the lower half of the clamshell housing by fasteners 116, 116*a*. Clamshell housing 100 is openable via a hinge located near fastener 116*a*.

Figure 5:
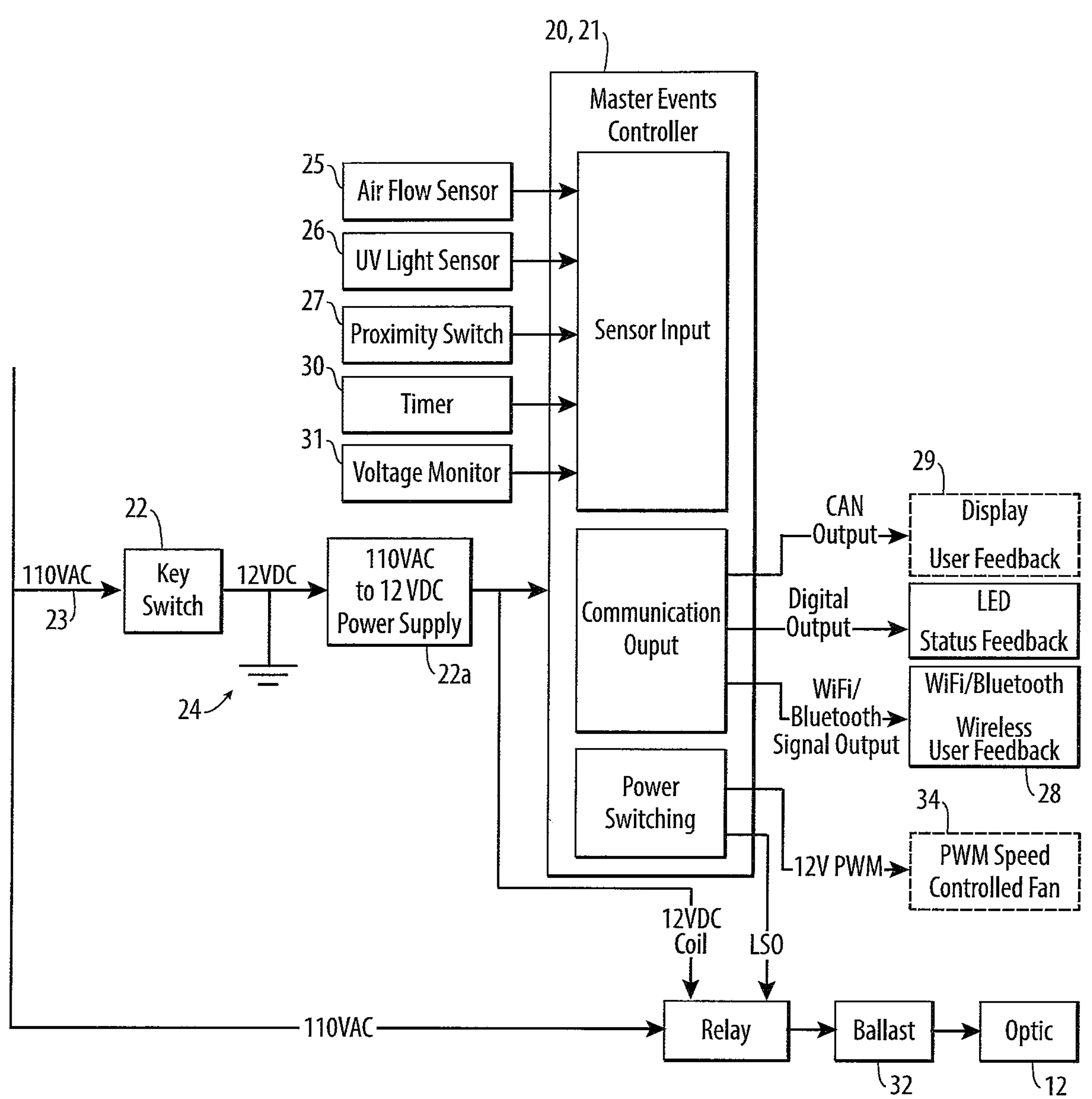
FIG. 5 is a block diagram of the electronic controls of the hydroxyl generator of FIGS. 1-3 and 4.

FIG. 5 is a block diagram showing the network and electronics of the control box 20. Initially AC power 23 of 110 VAC is converted by converter 22 to low voltage 12 VDC, or else a low voltage battery alternatively delivers 12 VDC to a secure Key Switch 22*a*, to provide power to the Master Events Controller 20, which may have a microprocessor 21. The Master Events Controller 20 also receives input from sensors, such as Air Flow Sensor 25, UV Light Sensor 26, Proximity Switch 27 (detecting opening of the enclosure), Timer 30 and Voltage Monitor Sensor 31. These sensors provide Sensor Input to the Master Events Controller 20. Power Switching in the Master Events Controller 20 sends 12V Pulse Width Modulation data to a PWM Speed Controlled Fan 34, to send air through the hydroxyl generator unit 1 or 101, or to stop the flow of air when needed for safety and maintenance situations. The Power Switching also sends data via a Large Serve Outlet (LSO) to a Relay, which controls the Ballast 32, providing power to the Crystal UV Optics 12, which creates the needed hydroxyls within the hydroxyl generators 1 or 101. The Master Events Controller 20 also has a Communications Output, which can send data via a Controller Area Network (CAN) to a Visual Display 29 for user feedback. The Communications Output of the Master Events Controller 20 also sends digital data wirelessly as output to Status Feedback Units. The Communications Output of the Master Events Controller 20 also sends Wi-Fi/Bluetooth® Signal output to Wireless input devices 28 for Wireless user feedback during use.

Figure 5A:
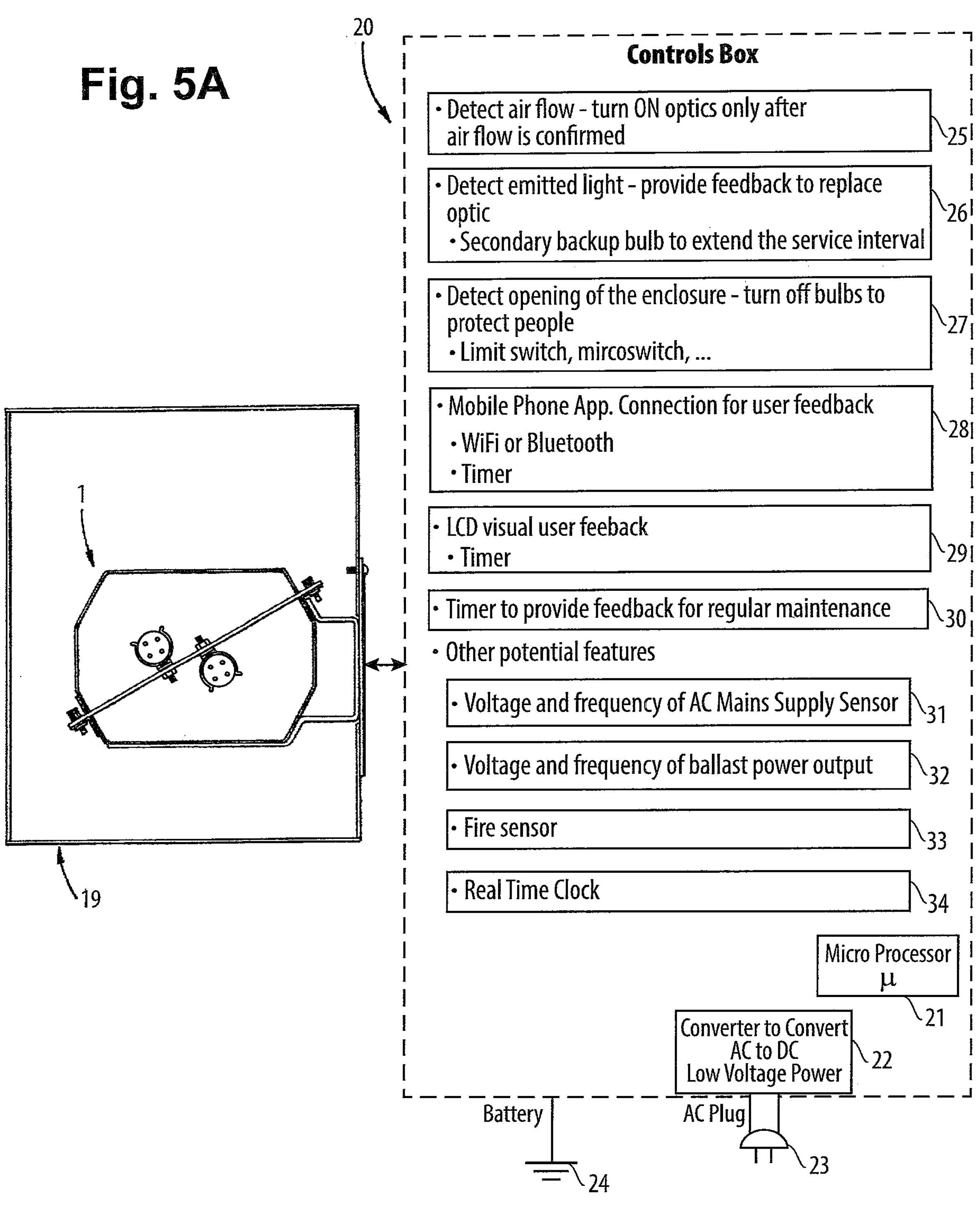
FIG. 5A is a flow chart showing the electronic controls with respect to their position adjacent to the hydroxyl generator.

FIG. 5A is a diagrammatic flow chart, showing the electronic control box 20 of FIGS. 1, 2 and 3, which is also equivalent to the electronic control box 120 of FIG. 4. Adjacent to the hydroxyl generator 1 or 101, which in FIGS. 1-3, the hydroxyl generators are attached by one or more brackets 19 to the electronic control box 20. Similarly, the electronic control box 120 is attached by brackets 119 of FIG. 4.

In the diagrammatic flow chart of FIG. 5A, related to the electrical block diagram of FIG. 5, the control box 20 includes a microprocessor 21 for controlling the sensors and switches, which control the operation of the optics 12 and 13, or 112 and 113, of the hydroxyl generators 1 shown in FIGS. 1-3 and 4 respectively. There is also a power source being either a DC low-voltage battery 24, or an AC plug 23, to provide higher-voltage AC power. When the AC is used, a converter 22 can be provided to convert high-voltage AC to low-voltage DC power for operating any of the sensors and control elements within box 20. Box 25 of FIG. 5A discloses the detector 25 to detect whether airflow is on, so that the optics 12 and 13 will only be on after airflow is confirmed, so that they are not on when there is no airflow. Box 26 of the diagrammatic flow chart of FIG. 5A discloses the sensor 26 for detecting emitted light, and providing feedback to replace optics, including a secondary backup optic, which is also disclosed in box 26 of the flowchart of FIG. 5A. Box 27 of the diagrammatic flow chart of FIG. 5A discloses a detector with a proximity switch 27 detecting opening of the enclosure, and thereafter used to turn off the optics 12 and 13, to protect people from being exposed to the possible harmful UV light emitted from the optics 12 and 13. This detector with the proximity switch 27 shown in box 27 of the diagrammatic flow chart of FIG. 5A also includes a limit switch, a micro switch and sensors. Box 28 of the diagrammatic flow chart of FIG. 5A discloses the mobile phone application connection 28 for user feedback by wireless communication, such as Wi-Fi or Bluetooth® communications, between the operator, the control box 20 and hydroxyl generator 1 itself, together with a timer. The control box 20 also includes the LCD user feedback system 29, with a timer shown in box 29 of the diagrammatic flow chart of FIG. 5A with a timer, as well as a further timer 30 shown in box 30 of the diagrammatic flow chart of FIG. 5A, to provide feedback for regular maintenance. The voltage and frequency of AC main supply sensor 31 is shown in box 31 of the diagrammatic flow chart of FIG. 5A, Box 32 of the diagrammatic flow chart of FIG. 5A shows the voltage and frequency of the monitor of the ballast power outfit 32. Box 33 of the diagrammatic flow chart of FIG. 5A discloses a fire sensor 33, which detects excess heat in the system. Box 34 of the diagrammatic flow chart of FIG. 5A discloses a real time clock 34 which controls any fans providing and activating the airflow through the polygon hydroxyl generators 1.

In the mass transit vehicle applications, where a self-contained hydroxyl generator is located on the floor below a passenger seat, the primary source of power from the vehicle may be low voltage (12 VDC) which can be accompanied by a DC/AC inverter to convert the low voltage (12 VDC) to higher 120V AC power to operate the hydroxyl generator within the mass transit vehicle.

Figure 5B:
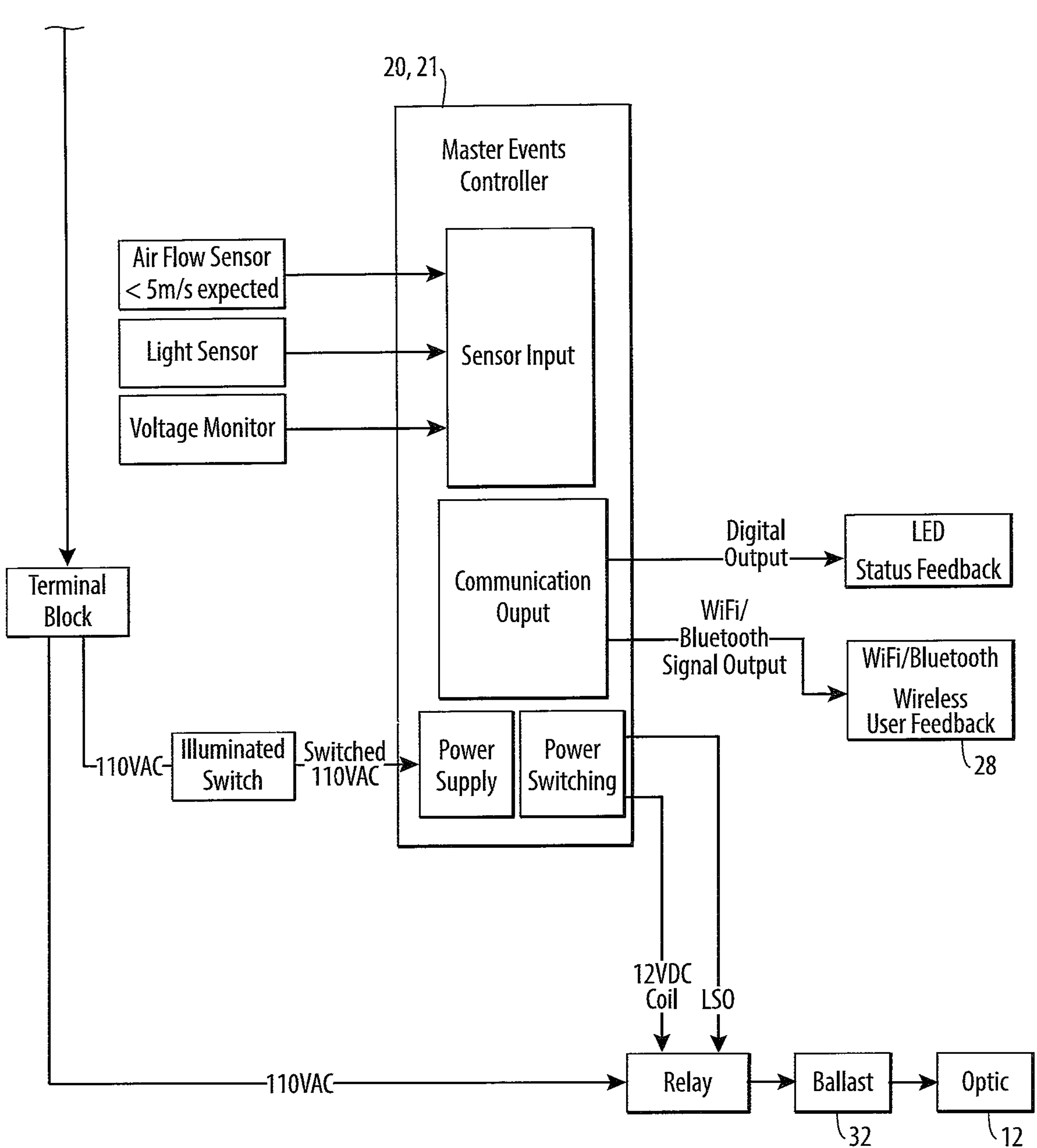
FIG. 5B is a block diagram of the electronic controls of the hydroxyl generator used in hydroponic greenhouse applications shown in FIGS. 6 and 6A, or in other applications requiring the electronic controls of FIG. 5B.
Figure 5C:
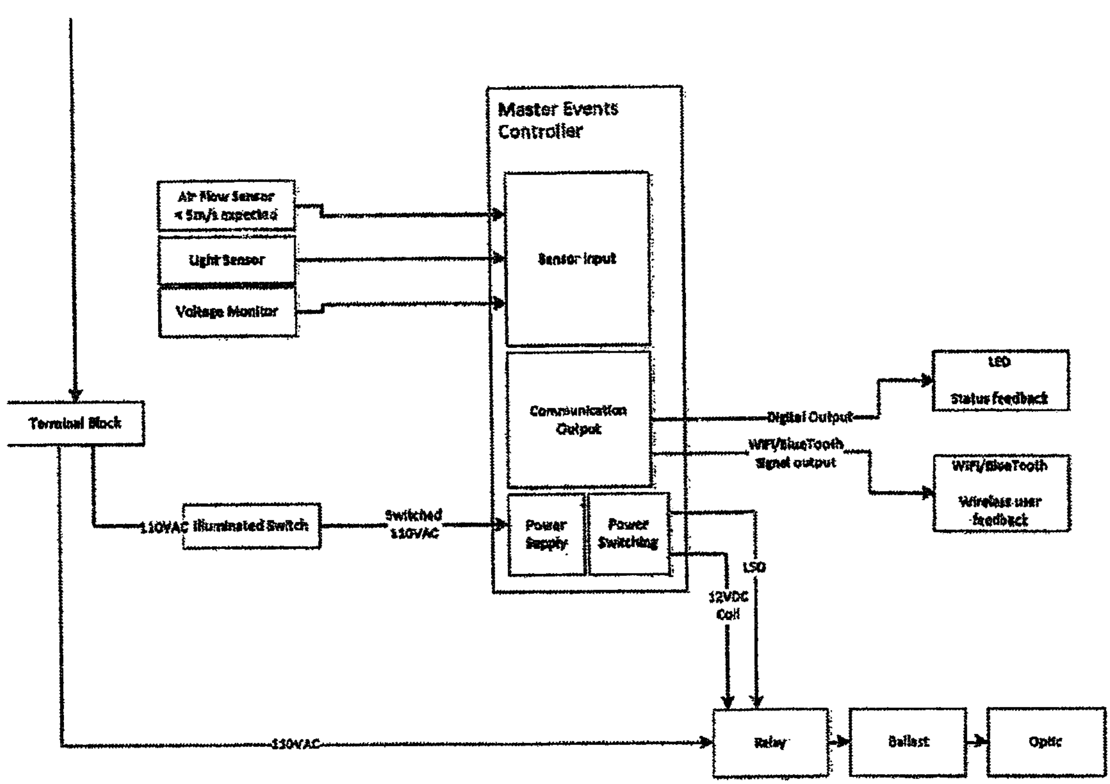
FIG. 5C is a block diagram of the electronic controls of the hydroxyl generator used in HVAC building duct applications, or in other applications requiring the electronic controls of FIG. 5C.
Figure 5D:
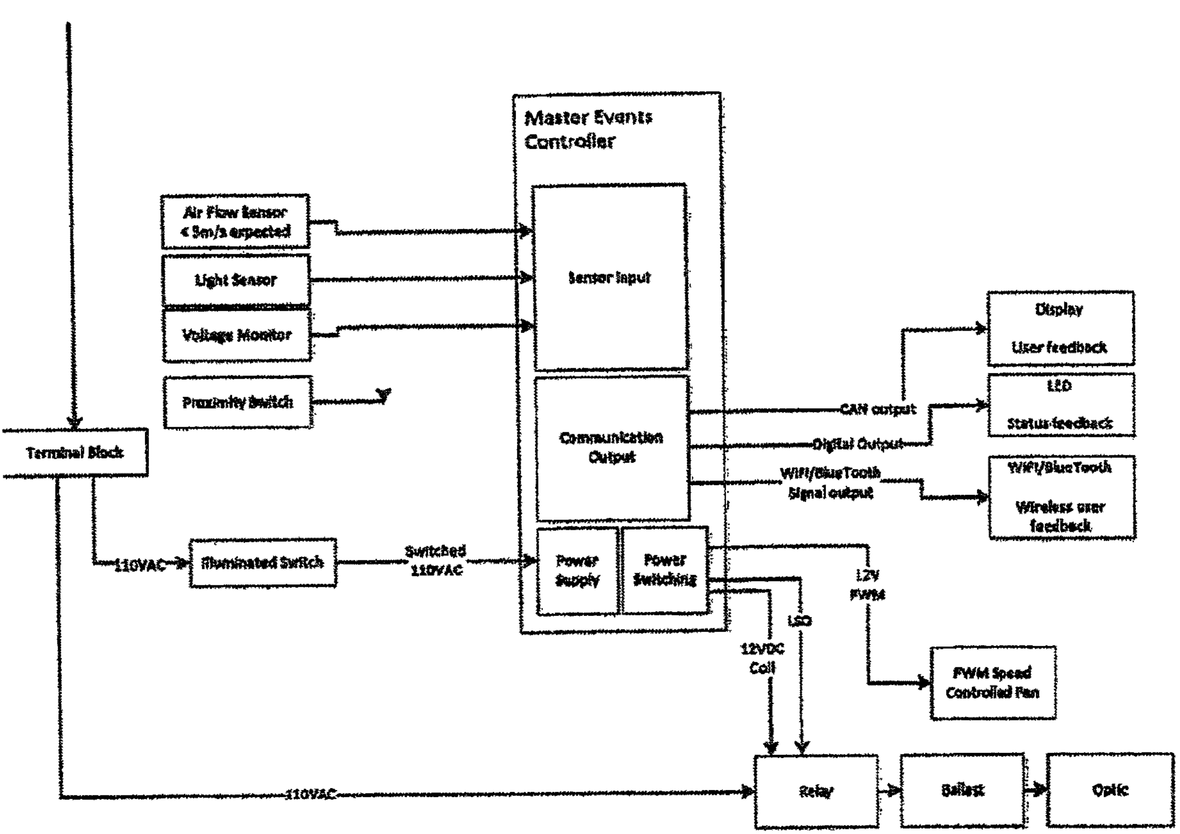
FIG. 5D is a block diagram of the electronic controls of the hydroxyl generator used in Portable Room-Sized Unit applications, or in other applications requiring the electronic controls of FIG. 5D, which include a proximity detector for safety reasons and a fan, such as a pulse width modulated fan, which regulates the air speed of the fan by regulating the voltage of the fan between on and off, to move air flow with air purifying generated hydroxyl radicals therethrough.

In the alternate embodiment shown in block diagram FIG. 5B, there are disclosed therein shown the following differences of block diagram FIG. 5B from block diagram FIG. 5, wherein in block diagram FIG. 5B the following features are shown:

1. The key switch (22*a*) can alternatively be positioned before the power supply (22);
2. The key switch (22*a*) can alternatively be a pushbutton;
3. The power supply (22) can alternatively be included in the Master Events Controller (MEC) 20;
4. The user feedback display (29) of FIG. 5 is not needed in FIG. 5B, because the Wi-Fi/Bluetooth® communication works with a mobile application;
5. The PWM Speed controlled fan (34) of FIG. 5 is not needed, because the hydroxyl generator 1 will be located in an existing duct with moving air; and,
6. The power to the relay (not numbered) in FIG. 5 can alternatively be provided by the Master Events Controller (MEC) 20 in FIG. 5B.

EXAMPLE

Transit Vehicle Embodiment

FIGS. 6, 6A, 6B, 6C, 6D, 6E, 6F and 6G show self-contained units 700 and 791 which can be provided within the passenger and/or cargo area 780 of a transit vehicle, which will have a smaller interior volume for producing the optimal number of hydroxyls generated to purify the air/surfaces and crevices/creases within the aforesaid areas. Such a self-contained hydroxyl generator 700 for a transit vehicle includes a generator chamber housing 701, which is mounted inside a transit vehicle.

Figure 6:
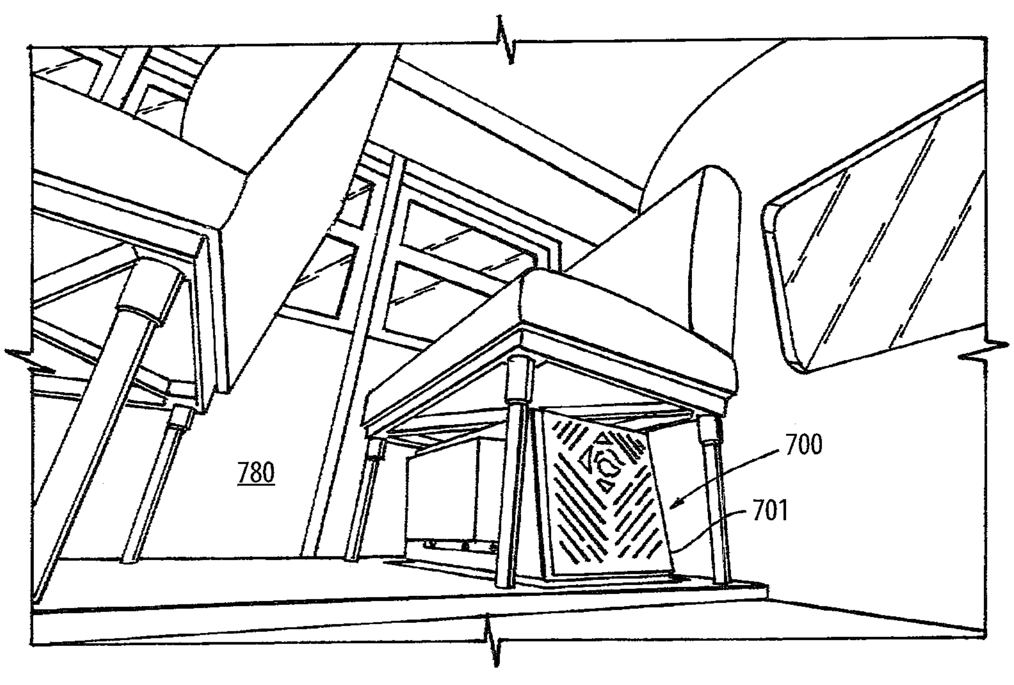
FIG. 6 is a perspective environmental view of the hydroxyl generator in use in a transit vehicle, where the hydroxyl generator is shown in a self-contained housing below a seat of the transit vehicle.
Figure 6A:
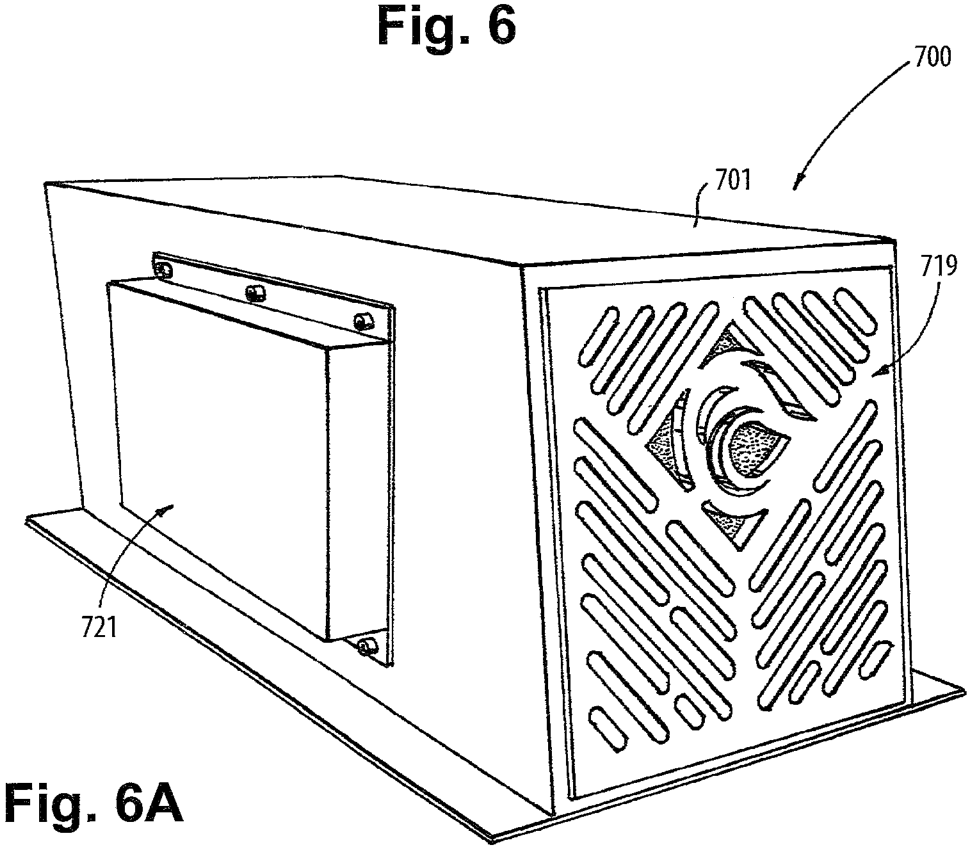
FIG. 6A is a perspective view of the housing for the hydroxyl generator of FIG. 6.
Figure 6B:
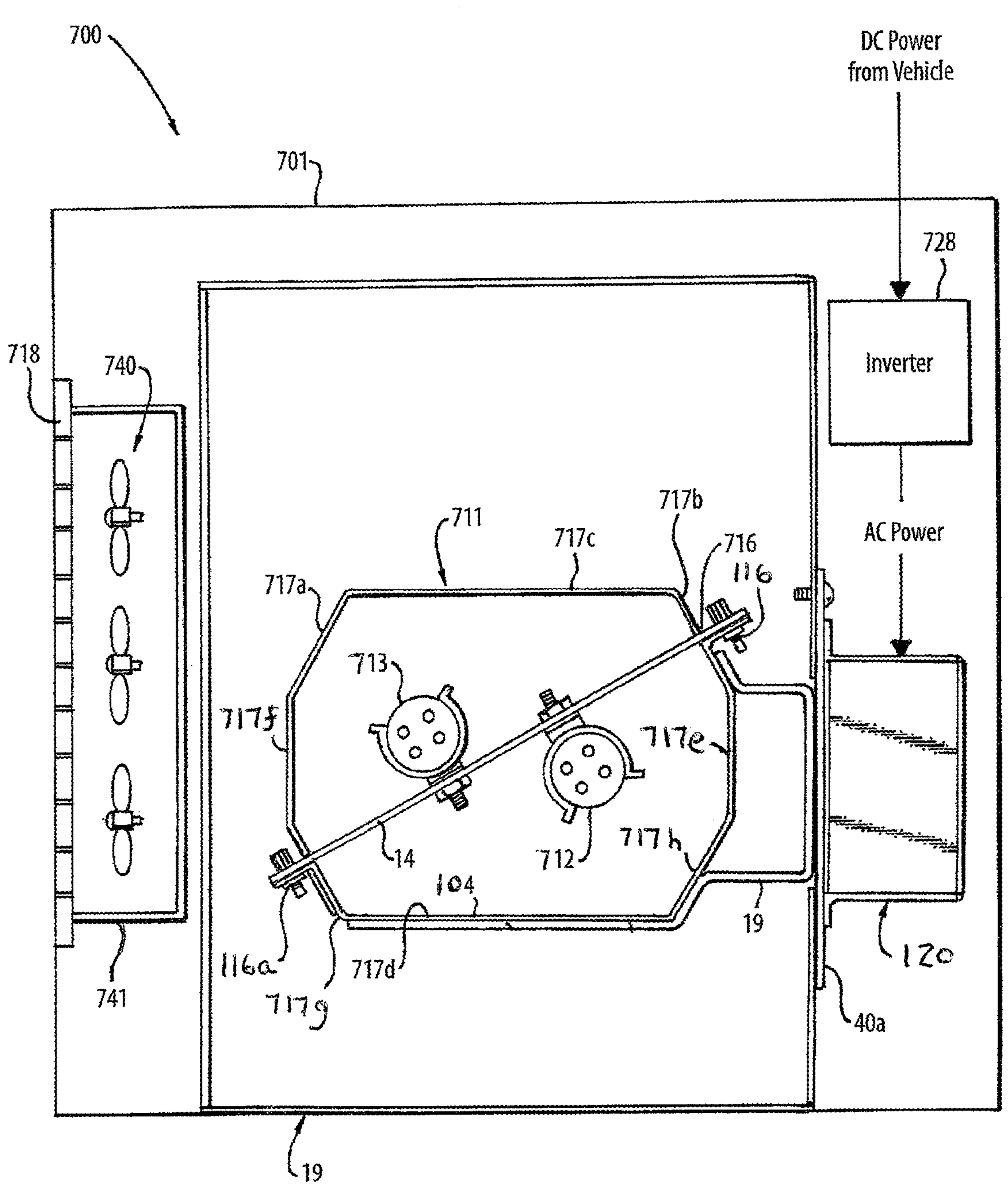
FIG. 6B is a cross-sectional end view of the hydroxyl generator of FIGS. 6 and 6A showing the clamshell housing having oppositely placed optics within the self-contained housing and connected to the control box within the outer self-contained housing of the hydroxyl generator and where an inverter is provided to convert the normal 12 volt DC voltage from the vehicle power supply to AC power as required for the hydroxyl generator to operate.
Figure 6C:
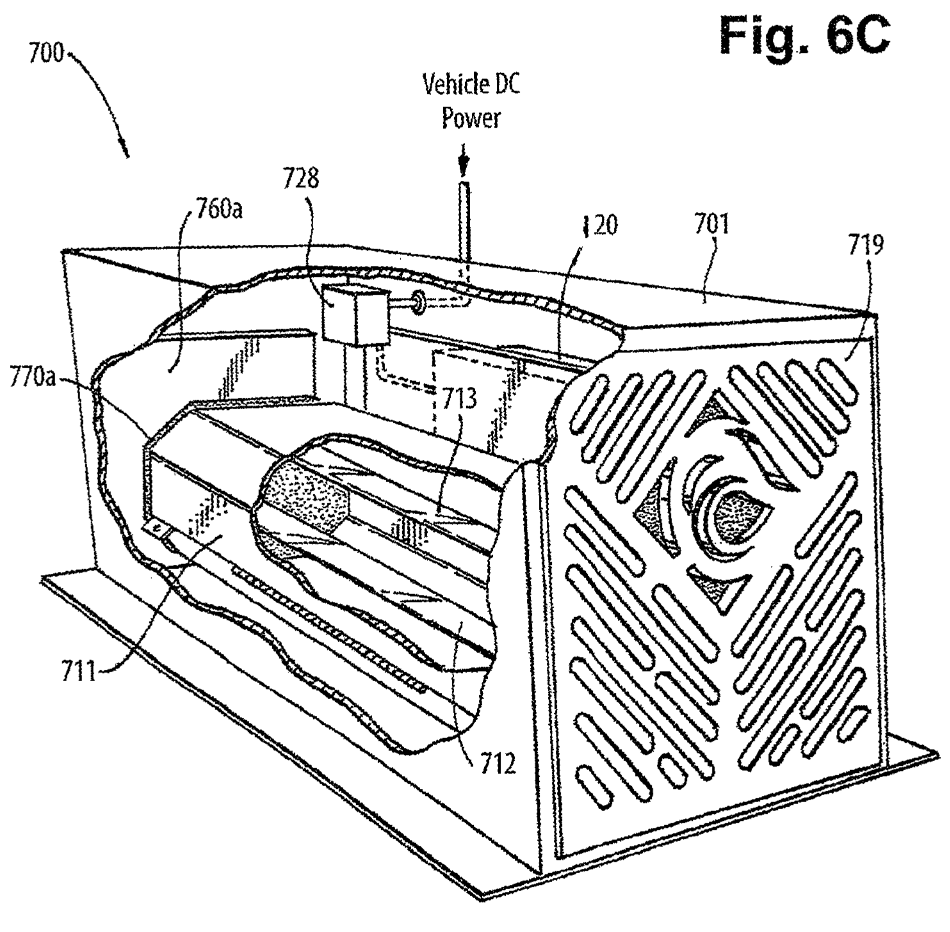
FIG. 6C is a perspective view in partial open cutaway cross-sectional view, exposing the interior components including the horizontally oriented polygonal clamshell unit with light producing optics as in FIG. 6B, the DC power supply input from the vehicle, and the DC to AC inverter for supplying AC power to the control box of the hydroxyl generator.

For example, FIG. 6 shows the generator housing 701 located on the floor of the vehicle below a passenger seat where the hydroxyl generator 700 is provided in a confined space area, such as a passenger cabin with seats or a cargo container with or without shelving.

Since the transit vehicle generates low voltage 12 DC for vehicle accessories (lights, wipers, cell phone chargers, etc.), the DC power is now converted to AC by an inverter 728 to power the optics and fans of the self-contained hydroxyl generator 700.

The transit vehicle generator 700 also includes the polygon generator chamber housing 701, which has inside the optics 712, 713, which react with water vapor within incoming airflow to produce hydroxyl radicals which are excited by exposure to the interior polygonal walls of the generator 700. The transit vehicle hydroxyl generator 700 also includes an air intake 719, as well as a partition and closed compartment space 720 for the electronics, and an air blower 740 which blows and pressurizes air to the chamber of the hydroxyl generator 701. Front frame 721 is provided for controls and the air intake 719 is provided on one of the walls of the housing 701, enclosing the clamshell shaped polygonal hydroxyl generator unit 711, which is enclosed within housing 701. The clamshell shaped polygonal hydroxyl generator unit 711 is preferably made of aluminum, or other suitable material. The clamshell shaped polygonal hydroxyl generator unit 711 has side walls 717*a*, 717*b*, 717*g*, 717*h*, top wall 717*c* and bottom wall 717*d*, as well as rear wall 717*e* and front cover 717*f* When the aluminum cover 717*c* is removed, it provides easy access for optic cleaning and/or replacement of the optics of the hydroxyl generator 700, which can be taken out and opened along its clamshell hinge 716. The air is passed through the intake, blown by the blower 740, then through the polygonal generator chamber housing 701 and out through an air outlet 718. The blower 740 is mounted by a mount 741 to the exterior housing 701 of the hydroxyl generator 700.

Figure 6D:
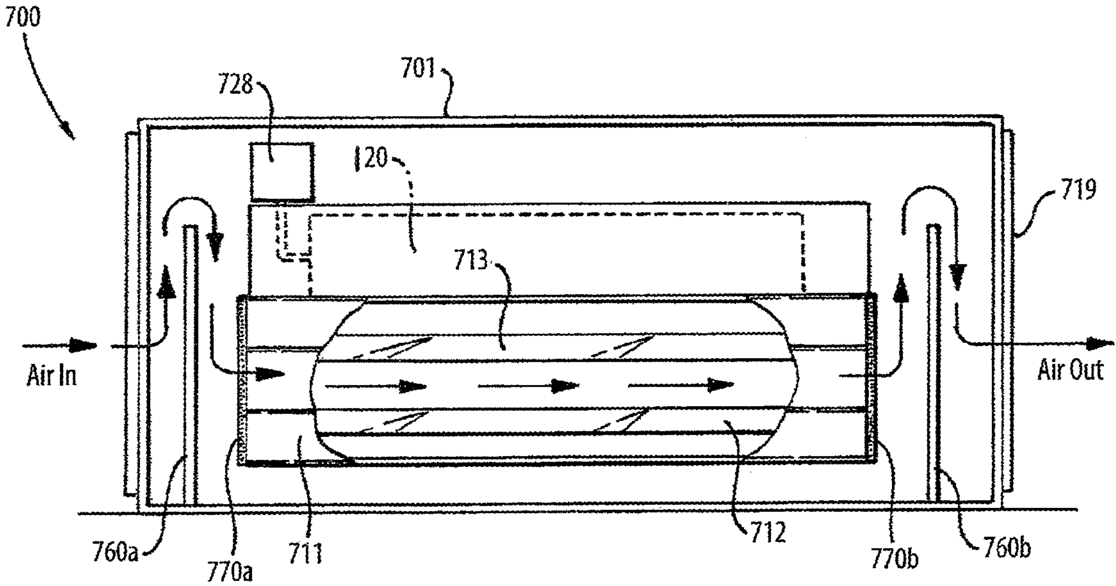
FIG. 6D is a diagrammatic side view in cross-section of the hydroxyl generator for transit vehicles, showing the "S-curve" diversion of the airflow by light blocking baffles provided at the intake forward entry end and at the exit aft end of the hydroxyl generator housing, to block inadvertent eye damaging light emanating from the concealed optics in the hydroxyl generator housing, while air filters are also provided at the forward entry end and exit aft end of the hydroxyl generator housing, to filter out any dirt or undesirable airborne particles that might tend to degrade the sensitive medical grade pure quartz material of the optics.

FIG. 6D shows a side view in cross-section of the hydroxyl generator 700 for transit vehicles, showing the “S-curve” diversion of the incoming and outgoing airflow “A”, which diversion is achieved by light blocking baffles 760*a* and 760*b*, where one or more staggered baffles 760*a*, 760*b* are at the air flow exit portion of the hydroxyl generator housing 701 for transit vehicles and one or more staggered baffles 760*a*, 760*b* are at the air flow entry point of the hydroxyl generator housing 701. The staggered baffles 760*a*, 760*b* are configured to block inadvertent eye-damaging light emanating from the hydroxyl generator housing, especially for curious short children or leased service dogs for people in need of canine assistance while traveling in a transit vehicle, who might tend to stare and look at the hydroxyl generator 700, located on the floor under a passenger seat of the passenger cabin 780 of a transit vehicle. A generator mounting bracket 119 may be used to secure the hydroxyl generator 1 to an interior surface of a side wall of the housing 701, and as seen in FIG. 6D, a first end of the generator housing may be positioned at a first distance away from a first end of the housing, with a second end of the generator housing being positioned at a second distance away from the second end of the housing, such that the second distance may be about the same as the first distance.

FIG. 6D also shows filters 770*a* and 770*b*, which are provided at the air flow entry and exit locations within the hydroxyl generator housing 701, to protect the optics 712, 713 etc. from contamination by airborne dirt and other particles which might accompany the incoming air flow and which may degrade the hydroxyl activation portions of the optics 712, 713, etc., which are made of sensitive medical grade pure quartz material.

Figure 6E:
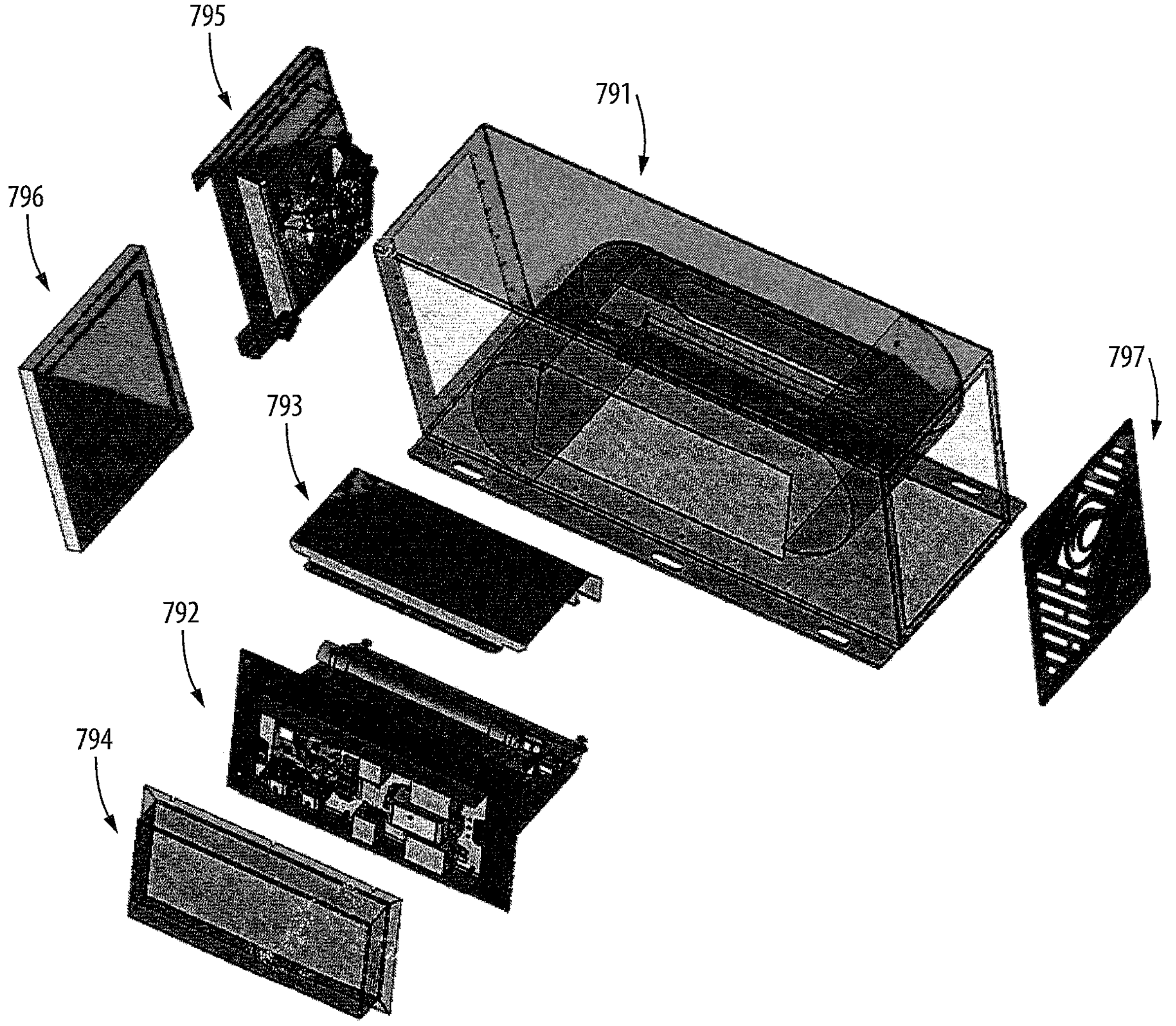
FIG. 6E is an exploded view of a stand-alone hydroxyl generator for transit vehicles with a three-pass air flow to limit UV light escape, where a clamshell hydroxyl generator reactor with a structural cover and an electronics cover, is insertable inside the housing in the open central area shown. The air input side of the unit includes a fan to move air with water vapor therethrough, and a filter is provided to prevent dirt, dust and other contaminating particles from compromising the sensitive quartz surfaces of the UV optics, which create hydroxyl radicals when water vapor from incoming air contacts the UV from the optics within the hydroxyl generator reactor portion. An exit grill is provided at the air exit end of the stand-alone hydroxyl generator, which is placed away from passenger standing or walking areas, within the confines of a transit vehicle, such as on the floor beneath one of more passenger seats in the transit vehicle.
Figure 6F:
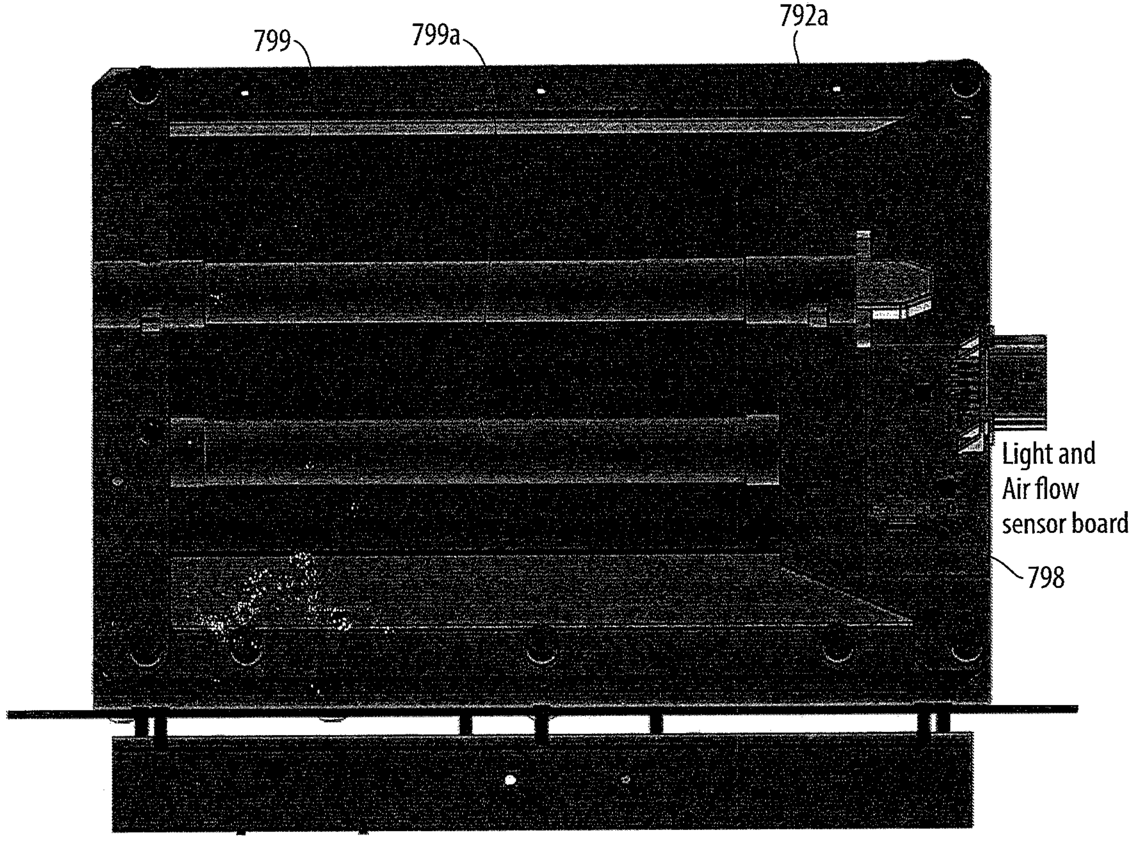
FIG. 6F is a side view in cross section of the hydroxyl generator reactor enclosure for transit vehicles, showing two UV producing optics and a light and air flow sensor board.
Figure 6G:
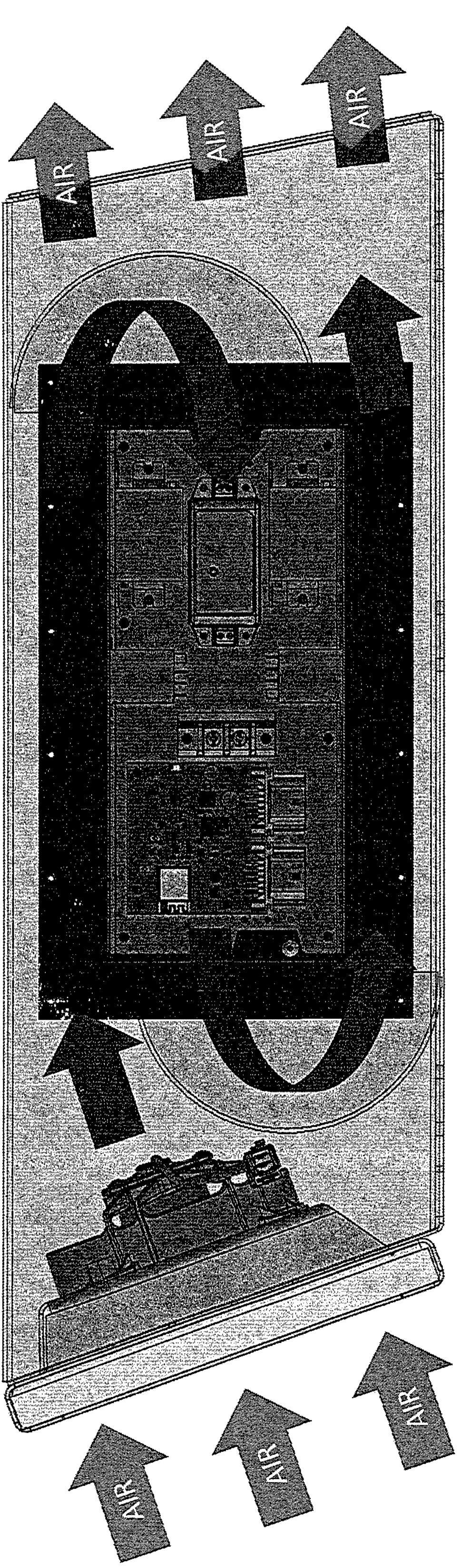
FIG. 6G is a side view in cross section of the hydroxyl generator of FIG. 6E, showing the air entry fan and the undulated "S shaped" air flow of the incoming air around the centrally located hydroxyl generator reactor, then through the hydroxyl generator reactor, and finally around the hydroxyl generator reactor in a different direction out of the stand-alone hydroxyl generator for mass transit vehicles.

The hydroxyl generators shown in FIGS. 6-6G will inactivate any VOCs or pathogens, such as virus, bacteria or fungi, anywhere in the air of the transit vehicles 780.

FIG. 6E is an exploded view of a preferred embodiment for a stand-alone hydroxyl generator 790 in a housing 791 for a transit vehicle with a three-pass air flow to limit UV light escape, where a clamshell hydroxyl generator reactor 792 with a structural cover 793 and an electronics cover 794, is insertable inside the housing 791 in the open central area shown. The air input side of the hydroxyl generator housing 791 includes a fan 795 to move air with water vapor therethrough, and a filter 796 is provided to prevent dirt, dust and other contaminating particles from compromising the sensitive quartz surfaces of the UV optics 799, 799*a*, which create hydroxyl radicals when water vapor from incoming air contacts the UV from the optics 799, 799*a* within the hydroxyl generator reactor portion 792 in an enclosure 792*a* having a light and air flow sensor board 798. An exit grill 797 is provided at the air exit end of the stand-alone hydroxyl generator 790, which is placed away from passenger standing or walking areas, within the confines of a transit vehicle, such as on the floor beneath one of more passenger seats in the transit vehicle. As seen in FIG. 6E for the housing 791 (and in FIG. 6C for housing 701), a first mounting flange and a second mounting flange formed on opposite sides of the bottom of the housing may be used to secure the housing to the floor of the vehicle below a passenger seat (see FIG. 6), using fasteners that may be received through a plurality of openings in each of the flanges (see e.g., the slotted openings in the flanges shown in FIG. 6E).

FIG. 6F is a side view in cross section of the hydroxyl generator reactor enclosure 792*a*, showing two UV producing optics 799, 799*a* and a light and air flow sensor board 798 attached thereto.

FIG. 6G is a diagrammatic side view in cross section of the air flow within the hydroxyl generator of FIG. 6E, showing the air entry fan and the undulated “S shaped” air flow of the incoming air around the centrally located hydroxyl generator reactor, then through the hydroxyl generator reactor, and finally around the hydroxyl generator reactor in a different direction out of the stand-alone hydroxyl generator for mass transit vehicles.

CONCLUSION

The hydroxyl generator systems of the present invention are designed to neutralize and destroy virus' everywhere safely and effectively, while purifying and sanitizing breathable heated, ambient, or cooled air emanating from a source and neutralizing up to 99.9999% of tested virus, including Covid-19 virus. The present invention also helps occupants an occupied space who are afflicted with asthma and airborne allergies, including full air and surface protection, including in crevices between other surfaces.

The hydroxyl generator systems of the present invention can be placed in any environment where pristine air is required, in a state of the art technology that is chemical free, safe for people, pets and plants.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

What is claimed:

1. An air cleaning apparatus configured to be installed and to operate within an occupied enclosed interior space of a mass transit bus, said air cleaning apparatus comprising:

- a main housing, said main housing comprising: a hollow rectangular cross-sectional shape formed of a top wall, a bottom wall, a first side wall, and a second side wall that form an opening at each of a first end and a second end of said main housing;
- wherein said first side wall and said second side wall of said main housing each comprise: a height configured to fit between a bottom of a passenger seat and a floor surface of the mass transit bus when said air cleaning apparatus is mounted to the floor under the seat of the mass transit bus;
- wherein each of said top wall, said bottom wall, said first side wall, and said second side wall comprise: a length configured to underlie the seat without extending beyond a medial end of the seat, when said air cleaning apparatus is mounted to the floor under the seat of the mass transit bus;
- wherein each of said top wall and said bottom wall comprise: a width configured to underlie the seat without extending beyond a forward-facing end of the seat, when said air cleaning apparatus is mounted to the floor under the seat of the mass transit bus;
- a first mounting flange configured to extend away from a first side of said bottom wall, said first mounting flange comprising: a plurality of openings each configured to receive a respective fastener to mount a first side of said air cleaning apparatus to the floor of the bus;
- a second mounting flange configured to extend away from a second side of said bottom wall, said second mounting flange comprising: a plurality of openings each configured to receive a respective fastener to mount a second side of said air cleaning apparatus to the floor of the bus;
- a hydroxyl generator, said hydroxyl generator comprising:
  - a generator housing, said generator housing comprising: a linearly elongated octagonal cross-sectional shape having an opening at and between each of its first end and its second end to form a chamber, and a reflective interior surface;
  - a plurality of UV lamps each mounted to said generator housing and suspended therein with an axis of a bulb of each lamp mounted parallel to a direction of said linearly elongated octagonal cross-sectional shape of said generator housing;

wherein each of said plurality of UV lamps is configured to emit one or more wavelengths of ultraviolet light being in the range of 100 nm to 400 nm;

a first generator filter, said first generator filter mounted to said first end of said generator housing, to thereby filter air passing into or out from said first end of said generator housing;

a second generator filter, said second generator filter mounted to said second end of said generator housing, to thereby filter air passing into or out from said second end of said generator housing;

a generator mounting bracket, said generator mounting bracket configured to secure said hydroxyl generator to an interior surface of said first side wall of said main housing, with a first end of said generator housing being positioned at a first distance away from said first end of said main housing, with a second end of said generator housing being positioned at a second distance away from said second end of said main housing, with a bottom surface of said octagonal shape of said generator housing being positioned a third distance away from said bottom wall of said main housing, and with a top surface of said octagonal shape of said generator housing being positioned a fourth distance away from said top wall of said main housing;

an exit grill, said exit grille mounted to, and configured to cover, said second end of said main housing;

wherein said exit grill comprises: a plurality of openings configured to admit passage of air therethrough;

an air blower, said air blower configured to blow and pressurize air into said chamber of said generator housing;

wherein said one or more wavelengths of ultraviolet light emitted by said plurality of UV lamps create hydroxyl radicals from water vapor contained within the pressurized air blown into said chamber of said generator housing that exit said plurality of openings in said exit grille and react with and inactivate impurities including volatile organic compounds, viruses, bacteria, and mold in the pressurized air and the interior surfaces of the bus.

2. The air cleaning apparatus of claim 1, wherein said plurality of UV lamps are positioned in an asymmetric, staggered arrangement across a width of said generator housing.

3. The air cleaning apparatus of claim 2, further comprising:

a first baffle, said first baffle positioned between said first end of said generator housing and said first end of said main housing, and being sized to block the one or more wavelengths of ultraviolet light emitted by said UV lamp from being emitted directly out said first end of said main housing;

a second baffle, said second baffle positioned between said second end of said generator housing and said second end of said main housing, and being sized to block the one or more wavelengths of ultraviolet light emitted by said UV lamp from being emitted directly out said second end of said main housing.

4. The air cleaning apparatus of claim 3, further comprising:

an inverter, said inverter configured to receive 12 VDC power from the bus, and to convert the received power to alternating current to power said air blower and said plurality of UV lamps.

5. The air cleaning apparatus of claim 4, further comprising:

a control box, said control box being mounted adjacent said hydroxyl generator, said control box including a microprocessor for controlling sensors and switches which control operation of said said plurality of UV lamps within said hydroxyl generator.

6. The air cleaning apparatus of claim 5, further comprising:

a main filter, said main filter mounted to said first end of said generator housing, to thereby filter air passing into said first end of said generator housing; and wherein said air blower is positioned between said main filter and said first generator filter.

7. The air cleaning apparatus of claim 6, wherein said generator housing is formed of aluminum.

8. The air cleaning apparatus of claim 7, wherein said second distance is the same as said first distance.

* * * * *